US012759952B2

(12) United States Patent
de Smit et al.

(10) Patent No.: US 12,759,952 B2
(45) Date of Patent: Oct. 13, 2026

(54) METATHESIS OF $C_4/C_5$ TO PROPYLENE AND 1-HEXENE

(71) Applicant: ExxonMobil Chemical Patents Inc., Baytown, TX (US)

(72) Inventors: Emiel de Smit, Brussels (BE); Robert B. Larson, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 158 days.

(21) Appl. No.: 18/684,771

(22) PCT Filed: Jul. 19, 2022

(86) PCT No.: PCT/US2022/037574
§ 371 (c)(1),
(2) Date: Feb. 19, 2024

(87) PCT Pub. No.: WO2023/022828
PCT Pub. Date: Feb. 23, 2023

(65) Prior Publication Data
US 2025/0002428 A1 Jan. 2, 2025

Related U.S. Application Data

(60) Provisional application No. 63/235,509, filed on Aug. 20, 2021.

(51) Int. Cl.
*C07C 6/04* (2006.01)
*C07C 5/333* (2006.01)

(52) U.S. Cl.
CPC ................ *C07C 6/04* (2013.01); *C07C 5/333* (2013.01)

(58) Field of Classification Search
CPC .................................. C07C 6/04; C07C 5/333
See application file for complete search history.

(56) References Cited

U.S. PATENT DOCUMENTS

| | | | | |
|---|---|---|---|---|
| 6,580,009 | B2 | 6/2003 | Schwab et al. | 585/324 |
| 6,727,396 | B2 * | 4/2004 | Gartside | C07C 11/107 585/324 |
| 6,777,582 | B2 | 8/2004 | Gartside et al. | 585/324 |
| 8,704,029 | B2 | 4/2014 | Nicholas et al. | 585/646 |
| 9,422,209 | B2 | 8/2016 | Stanley et al. | C07C 6/04 |
| 2001/0003140 | A1 | 6/2001 | Schwab et al. | 585/644 |
| 2005/0124839 | A1 | 6/2005 | Gartside et al. | 585/643 |

(Continued)

FOREIGN PATENT DOCUMENTS

FR 3015477 6/2015 ........... C07C 5/3337

OTHER PUBLICATIONS

*Chemical and Engineering News*, v.63(5), p. 27 (1985).

*Primary Examiner* — Ellen M Mcavoy
(74) *Attorney, Agent, or Firm* — WOMBLE BOND DICKINSON (US) LLP; Kevin Davis

(57) ABSTRACT

A method, including: at least partially dehydrogenating a mixed alkane stream, including at least $C_4$ and $C_5$ alkanes, to generate at least a partial alkene stream and hydrogen; applying a metathesis reaction to the at least partial alkene stream to generate an effluent, wherein the metathesis reaction is optionally conducted in a presence of ethylene; and separating the effluent from the metathesis reaction into propylene, and 1-hexene.

15 Claims, 2 Drawing Sheets

(56) References Cited

U.S. PATENT DOCUMENTS

| | | | | |
|---|---|---|---|---|
| 2011/0034747 | A1* | 2/2011 | Gartside | C07C 4/04 585/326 |
| 2011/0245570 | A1* | 10/2011 | Nicholas | C07C 6/04 585/653 |
| 2011/0263917 | A1* | 10/2011 | Van Hal | C07C 2/76 585/322 |
| 2013/0172647 | A1* | 7/2013 | Coleman | C07C 11/08 585/329 |
| 2014/0121429 | A1* | 5/2014 | Coleman | C07C 6/04 585/315 |
| 2014/0194659 | A1* | 7/2014 | Hood, Jr. | C07C 6/04 585/324 |
| 2015/0141721 | A1* | 5/2015 | Choi | C07C 6/04 585/326 |
| 2020/0071245 | A1* | 3/2020 | Evitt | C07C 5/2556 |

* cited by examiner

METATHESIS OF $C_4$/$C_5$ TO PROPYLENE AND 1-HEXENE

CROSS REFERENCE TO RELATED APPLICATIONS

This application claims the benefit of and priority to U.S. Provisional Application No. 63/235,509 filed Aug. 20, 2021, the disclosure of which is incorporated herein by reference.

TECHNICAL FIELD

Exemplary embodiments described herein relate to a process and system for the simultaneous production of propylene and 1-hexene from a mixed $C_4$/$C_5$ alkane stream.

BACKGROUND

European patent document EP2895445, the subject matter of which is hereby incorporated by reference in its entirety, describes a process for producing propylene, including: fractionating a mixed $C_4$ hydrocarbon stream to recover a first fraction comprising isobutene and a second fraction comprising 2-butene; contacting the first fraction with a first metathesis catalyst in a first metathesis reaction zone; recovering an effluent from the first metathesis reaction zone comprising at least one of ethylene, propylene, unreacted isobutene, $C_5$ olefins, and $C_6$ olefins; contacting the second fraction and the ethylene in the effluent with a second metathesis catalyst in a second metathesis reaction zone; recovering an effluent from the second reaction zone comprising at least one of unreacted ethylene, propylene, unreacted 2-butene, fractionating the effluent from the first metathesis reaction zone and the effluent from the second metathesis reaction zone to recover an ethylene fraction, a propylene fraction, one or more $C_4$ fractions, and a fraction comprising at least one of $C_5$ and $C_6$ olefins.

European patent document EP1831135, the subject matter of which is hereby incorporated by reference in its entirety, describes a process for producing propylene from a $C_4$ feed containing 2-butene, which includes contacting said feed with ethylene in a metathesis reaction zone containing a metathesis catalyst under metathesis reaction conditions to provide an effluent including propylene, said metathesis catalyst consisting essentially of a transition metal or oxide thereof supported on a high purity silica support possessing less than about 150 ppm magnesium, less than about 900 ppm calcium, less than about 900 ppm sodium, less than about 200 ppm aluminum, and less than about 40 ppm iron.

European patent document EP2552871, the subject matter of which is hereby incorporated by reference in its entirety, describes a process for the conversion, under conditions and with a catalyst system effective for olefin metathesis, of hydrocarbon feedstocks comprising butylene, for example all or a large proportion of a single $C_4$ olefin isomer such as butene-1, are described. Olefin products, and particularly propylene, are formed in the presence of a catalyst comprising a solid support and a tungsten hydride bonded to alumina present in the support. This occurs despite the expectation that the olefin metathesis reaction mechanism leads to the formation of olefin products having other carbon numbers.

French patent document FR3015477, the subject matter of which is hereby incorporated by reference in its entirety, describes a process for producing propylene from a feedstock comprising linear paraffins having a carbon number of from 8 to 30, said process comprising: a) a step of selective dehydrogenation of the linear paraffins of the feed, b) a step of isomerization and metathesis, in the presence of ethylene, linear monoolefins contained in the effluent from step a), c) a step of separating the effluent from step b). FR3015477 only focuses on propylene production by metathesis using dehydrogenated linear $C_8$-$C_{30}$ parrafins as a feed).

European patent document EP1134271, the subject matter of which is hereby incorporated by reference in its entirety, describes a process for preparing propene and hexene from a raffinate II feed stream comprising olefinic $C_4$-hydrocarbons comprises a) a metathesis reaction in which butenes present in the feed stream are reacted with ethene in the presence of a metathesis catalyst comprising at least one compound of a metal of transition groups VIb, VIIb or VIII of the Periodic Table of the Elements to give a mixture comprising ethene, propene, butenes, 2-pentene, 3-hexene and butanes, using, based on the butenes, from 0.05 to 0.6 molar equivalents of ethene, b) firstly fractionally distilling the product stream obtained in this way to give a low-boiling fraction A comprising $C_2$-$C_3$-olefins and a high-boiling fraction comprising $C_4$-$C_6$-olefins and butanes, c) subsequently fractionally distilling the low-boiling fraction A obtained from b) to give an ethene-containing fraction and a propene-containing fraction, with the ethene-containing fraction being returned to the process step a) and the propene-containing fraction being discharged as product, d) subsequently fractionally distilling the high-boiling fraction obtained from b) to give a low-boiling fraction B comprising butenes and butanes, a pentene-containing intermediate-boiling fraction C and a hexene-containing high-boiling fraction D, e) where the fractions B and C are completely or partly returned to the process step a) and the fraction D is discharged as product.

EP1483224, the subject matter of which is hereby incorporated by reference in its entirety, describes that a $C_3$ to $C_6$ hydrocarbon cut from a cracking unit is processed for the conversion of olefins to propylene and hexene via autometathesis. The autometathesis of a mixed normal butenes feed in the presence of a metathesis catalyst operates without any ethylene in the feed mix to the metathesis reactor. Some fraction of the 2-butene feed may be isomerized to 1-butene and the 1-butene formed plus the 1-butene in the feed react rapidly with the 2-butene to form propylene and 2-pentene. The feed to the reactor also includes the recycle of the 2-pentene formed in the reactor with unreacted butenes to simultaneously form additional propylene and hexene. In one embodiment, some or all of the 3-hexene formed in the reaction is isomerized to 1-hexene. In another embodiment, some portion of the 3-hexene produced in the main metathesis reaction is reacted with ethylene to produce 1-butene without the need for superfractionation. In another embodiment, the 3-hexene product is hydrogenated and recycled back to the cracking heaters.

SUMMARY

A method, comprising: at least partially dehydrogenating a mixed alkane stream, including at least $C_4$ and $C_5$ alkanes, to generate at least a partial alkene stream and hydrogen; applying a metathesis reaction to the at least partial alkene stream to generate an effluent, wherein the metathesis reaction is optionally conducted in a presence of ethylene; and separating the effluent from the metathesis reaction into propylene and 1-hexene.

A system, comprising: a dehydrogenation unit configured to at least partially dehydrogenate a mixed alkane stream, including at least $C_4$ and $C_5$ alkanes, to generate at least a partial alkene stream and hydrogen; a metathesis unit configured to apply a metathesis reaction to the alkene stream to generate an effluent, wherein the metathesis reaction is optionally conducted in a presence of ethylene; and a separation unit configured to separate the effluent from the metathesis reaction into propylene and 1-hexene.

DETAILED DESCRIPTION

Definitions

Figure 1:
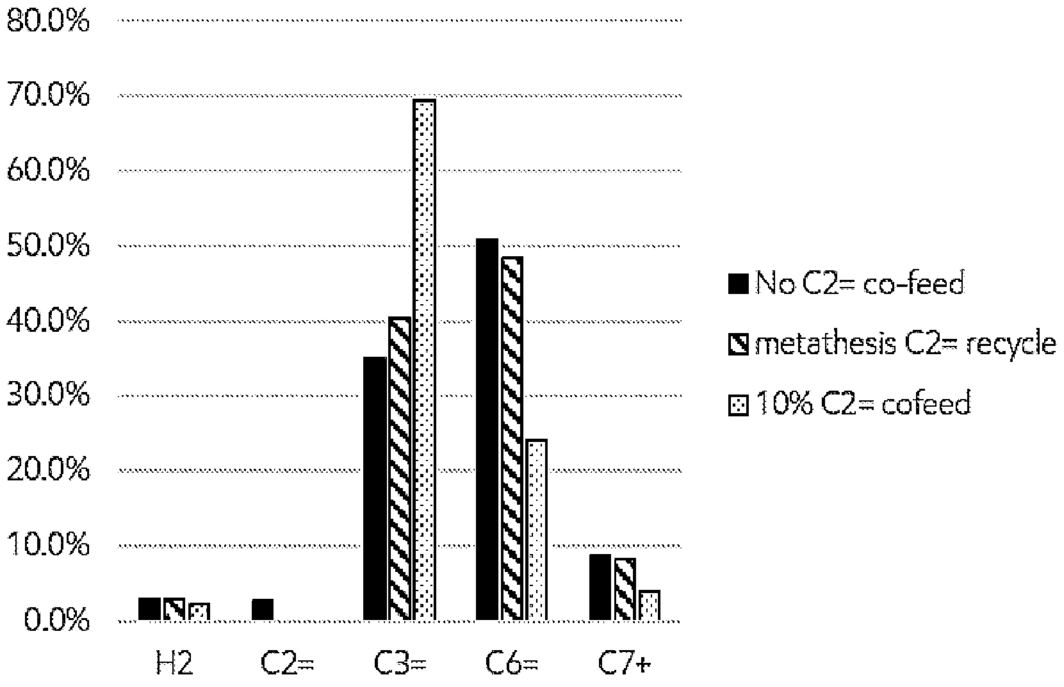
FIG. 1 is a graph illustrating how co-feeding ethylene can shift product distribution.

For the purposes of this invention and the claims thereto, the new numbering scheme for the Periodic Table Groups is used as described in *Chemical and Engineering News*, v.63(5), pg. 27 (1985). Therefore, a "group 4 metal" is an element from group 4 of the Periodic Table, e.g. Hf, Ti, or Zr.

As used herein, and unless otherwise specified, the term "$C_n$" means hydrocarbon(s) having n carbon atom(s) per molecule, wherein n is a positive integer.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. Likewise, a "Cm-Cy" group or compound refers to a group or compound comprising carbon atoms at a total number thereof in the range from m to y. Thus, a $C_1$-$C_{50}$ alkyl group refers to an alkyl group comprising carbon atoms at a total number thereof in the range from 1 to 50.

DESCRIPTION

Natural gas liquids (NGL) are hydrocarbons such as propane, ethane, butane, pentanes, and other condenstates ($C_{5+}$). They are hydrcocarbons removed (condensed) as a liquid from a hydrocarbon stream that is typically in a vapor phase (i.e., natural gas).

Propylene and 1-Hexene are important feedstocks for the chemical industry, with the majority being consumed for large scale polyolefin applications such as polypropylene and linear low density ethylene-1-hexene copolymers (polyethylene, LLDPE).

Conventional steam cracking is generally used to produce lighter alkenes, such as ethylene and propylene. Steam cracking produces more pounds of ethylene to pounds of propylene on a weight basis.

A typical full range linear alpha olefin (LAO) plant yields Schulz-Flory type ethylene oligomer distributions, and as a result, typically has a relatively low specific yield of 1-hexene, producing many other LAOs, such as 1-butene, 1-octenes and $C_{10+}$ LAOs in the process as major byproducts.

The present technological advancement advantageously can balance the above-noted mismatch of a steam cracker (low propylene) and an LAO plant (low 1-hexene) yield slate, and increase the yield of propylene and 1-hexene to meet growing market demand.

An embodiment of the present technological advancement can integrate the conversion of a mixed $C_4$ and $C_5$ alkane stream by dehydrogenation and subsequent metathesis into propylene and 1-hexene, where the final products are obtained by distillation (and isomerization to reach a higher yield of 1-hexene). Uncovered olefins can be recycled back to the metatheis reactor. Advantageously, embodiments of the present technological advancement can include some or all of the following features: (a) using a mixed $C_4/C_5$ feed to make $C_3^=$ and 1-$C_6^=$ simultaneously (whereas a conventional approaches (EP1134271 and EP1483224) only used $C_4$ olefins in the metathesis); (b) at least partially dehydrogenating the mixed $C_4/C_5$ (NGL) feed to alkenes before converting to alkanes in metathesis (FR3015477 ony focuses on propylene production by metathesis using dehydrogenated linear $C_8$-$C_{30}$ parrafins as feed); (c) using any other mixed $C_4/C_5$ alkane/alkene streams (e.g., FCC (fluid catalytic cracking, LLCN (light-light cracked naphtha), or other sources) for the combined production of propylene and 1-hexene; (d) passing a mixed $C_4/C_5$ (linear and brached) alkane/paraffin mixture through a metathesis reactor (without cofeeding $C_2^=$) to make two products ($C_3$= and 1-$C_6$=) simultaneously; (e) passing a mixed $C_4/C_5$ (linear and brached) alkane/paraffin mixture through a metathesis reactor while cofeeding $C_2^=$ to enhance $C_3^=$ yield vs. 1-$C_6^=$ yield as desired (conventional processes noted in the Background section describes using linear and highly olefinic feedstocks and not using mixed branched/linear and paraffinic/olefinic feedstock, wherein branched isomers and paraffins pass through the metathesis process and can be separated by distillation after the metathesis reactor and recycled back to the dehydrogenation reactor).

Olefin metathesis can be an attractive technology to convert heavier, less desirable olefins into ethylene and propylene, for which there is a larger market demand. For example, $C_4$ olefins can be converted to propylene using ethylene.

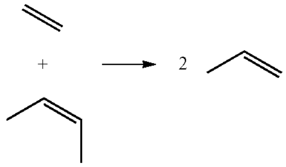

Conceptually, the present technological advancement can convert raffinate-2 from e.g. FCC units (or steam crackers) to propylene and therefore improve the overall $C_3$=: $C_2$=balance of olefin plants. In the same manner, mixed butenes (i.e. 1-butene and 2-butene) can also be converted to a mixture of ethylene, propylene, 2-pentene and 3-hexene.

The same metathesis chemistry also allows to make on-purpose 1-hexene (LLDPE co-monomer) from butenes:

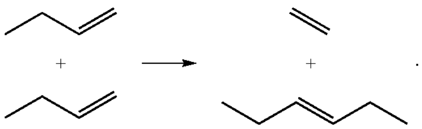

In this reaction, 3-hexene and ethylene are formed in the metathesis reaction from 1-butenes, and the 3-hexene is then isomerized into 1-hexene, 2-hexene and 3-hexene from which 1-hexene can be purified by distillation where the undesired other hexenes recycled to extinction.

Thus, conceptually, metathesis allows the conversion of terminal and internal olefins of a narrow (e.g. less desired, heavy) carbon number range into a mixture of terminal and internal olefins of a broader (including smaller, more desired) carbon number range.

The present technological advancement can integrate the conversion of $C_4$ and $C_5$ (e.g. NGL) feed into a mixed $C_4/C_5$ olefin stream, which is then converted by metathesis into mainly propylene and 1-hexene by distillation and recycling. The present technological advancement provides a way rectifying the propylene (in the case of steam cracker yield slate) and 1-hexene (in the case of full range LAO plant yield slate) production and market demand by the on-purpose production of propylene and 1-hexene from $C_4/C_5$ feeds.

Although exemplary embodiments of the present technological advancement focuses on the use of $C_4/C_5$ NGL feed, converted by dehydrogenation to provide the olefinic feed needed for the metathesis reaction, it is noted here that this process can also be applied to any existing olefinic $C_{4+}$ streams (FCC light cracked naphtha or raffinate, Steam cracker raffinate, butenes and pentenes from biomass sources, etc.).

Several olefin metathesis technologies have been commercialized (e.g. Shell Higher Olefin Process, Axens Meta-4, Lummus OCT) in the petrochemical industry but none have focused on the combined process of dehydrogenation and metathesis of mixed $C_4/C_5$ streams to produce mainly propylene and 1-hexene.

Although the emphasis of the present technological advancement is on the overall process and does not aim to claim any specific catalyst families or technologies to be used, it is noted that there is a broad range of catalyst technologies known to those of ordinary skilled in the art for the dehydrogenation and metathesis processes. There are several commercial (oxidative and non-oxidative) dehydrogenation processes developed for $C_4$ paraffins (IFP, Lummus, UOP), which can be applied to $C_{5+}$ paraffins as well. Common catalysts used in these processes are based on supported Pt, in combination with promoters (e.g. Sn, Ga, K, etc.) or based on supported V and Cr-oxides. A wide variety of heterogeneous catalysts, including W, Re or Mo oxides supported on basic oxides, such as MgO or CaO, or other conventional catalyst supports such as $SiO_2$, $Al_2O_3$, $ZrO_2$, $TiO_2$, $CeO_2$ etc. can be used for the metathesis reaction described here. In addition, the use of homogeneous (e.g. including but not limited to Grubbs or Schrock type) catalysts for metathesis is also in scope for this invention. In general, the present technological advancement is useable with any dehydrogenation or metathesis catalyst system.

The metathesis reaction conditions are conventional, and can include a temperature of from about 50° C. to about 600° C., preferably from about 200° C. to about 400° C., a weight hourly space velocity (WHSV) of from about 3 to about 200, preferably from about 6 to about 40, and a pressure of from about 10 psig to about 600 psig, preferably from about' 30 psig to about 100 psig. The reaction may be carried out by contacting the olefin(s) with the catalyst in the liquid phase, gas phase or mixed phase depending on structure and molecular weight of the olefin(s) and specific reactor conditions.

It is noted that branched olefins are less reactive (or unreactive) in the metathesis reaction and are expected to pass through the process unreacted. If desired, they can be removed from the process by etherification with methanol with potential use in fuel applications (e.g. as MTBE or TAME fuel additives) and/or converted back into a high purity branched olefin stream by subsequent cracking.

For the evaluation of the overall process, the expected stream compositions were modeled based on the parameters below. The $C_4/C_5$ olefin feed composition was based on typical NGL composition of 2:1 butanes to pentanes and equilibrium dehydrogenation conversion was assumed at 550° C. and 0.1 barg (yielding 50% conversion for butane and 60% conversion for pentanes and ~50-60% olefinicity of the stream after dehydrogenation). It is known that the metathesis reaction is a second order reaction with a statistical selectivity profile (e.g. the carbon number distribution primarily depends on the molar concentration of the reacting olefins). Therefore, to evaluate the expected metathesis product slate a simple statistical metathesis model was developed. To evaluate feasibility of the present technological advancement from product purity, distillation and recycle perspective, a simulation was built using process simulation software (PRO/II 10.1 SimSci).

Figure 2:
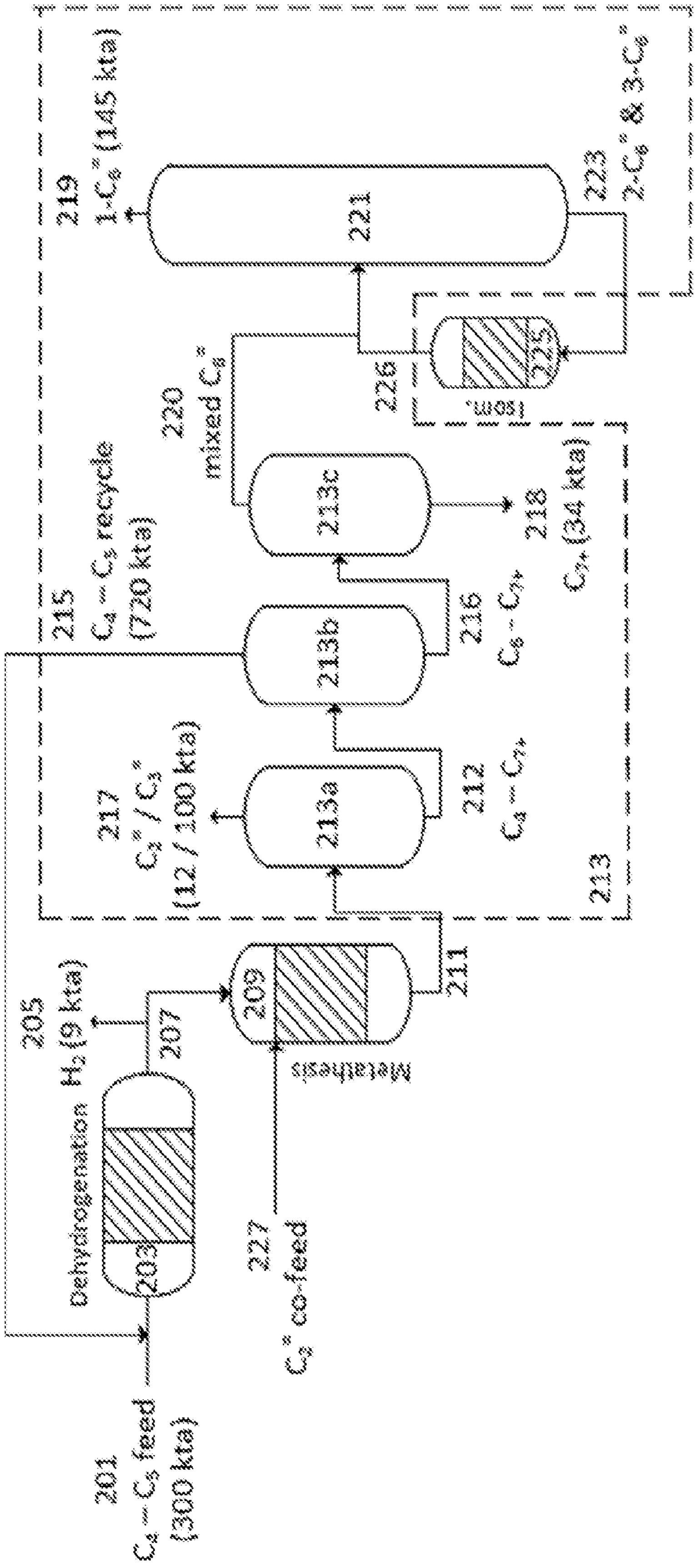
FIG. 2 illustrates an exemplary embodiment using a combination of dehydrogenation and metathesis to produce $C_3^=$ and 1-$C_6^=$.

The statistical metathesis model assumed that a i-$C_j$ olefin will react with a n-$C_m$ olefin to form a olefin of carbon number j+m−i−n and a second olefin of carbon number i+n. For example, 1-butene (1-$C_4$) will react with 2-pentene (2-$C_5$) to form a hexene and a propylene molecule. In this way, the (molar) concentration of the isomers in the feed were used to calculate the expected metathesis product distribution. $C_4$-$C_5$ paraffins and olefins were recycled through dehydrogenation and metathesis in the overall process simulation. The formed olefin isomers for $C_{4+}$ were assumed to be at thermodynamic equilibrium after the respective high temperature dehydrogenation and metathesis reactors (assuming dehydrogenation conditions of 550° C. and 0.1 barg and metathesis conditions of 300° C. and 0.1 barg). The distillation of the resulting metathesis reactor product stream was simulated using the configuration as shown in FIG. 2 and the process simulation software mentioned above. An example of the conditions and stream compositions from the simulation, assuming no co-feeding of ethylene, is shown in Table 1. For all distillation equipment, 30 trays and a reflux ratio of 3 was assumed and a specification of max. 0.1 wt. % of heavy products in the distillation overhead streams was set. It is noted that this is an example and that the distillation parameters can be further optimized to accommodate product purity and process and capital efficiency (e.g. heat integration and equipment sizing).

TABLE 1

| Products (kta) | No $C_2$ = co-feed (base case) | Metathesis $C_2$ = recycle (0.8% $C_2$=) | 5% $C_2$ = cofeed | 10% $C_2$ = cofeed | 20% $C_2$ = cofeed |
|---|---|---|---|---|---|
| $H_2$ | 8.8 | 8.8 | 7.8 | 7.1 | 6.6 |
| $C_2$= | 8.0 | | | | |
| $C_3$= | 105.0 | 120.8 | 172.3 | 208.5 | 249.0 |
| $C_6$= | 152.2 | 145.4 | 102.4 | 72.2 | 37.2 |
| $C_{7+}$ | 26.0 | 25.0 | 17.5 | 12.2 | 7.2 |
| Total | 300.0 | 300.0 | 300.0 | 300.0 | 300.0 |

From the model it was identified that co-feeding ethylene will significantly shift the product distribution (FIG. 1) towards propylene and other lighter olefin products, which will allow tuning the amount of hexene vs. propylene that is formed, which and can be exploited in process operation.

The base case here, assuming no co-feeding of ethylene, will maximize hexene yields but increase the size of the $C_4/C_5$ recycle and $C_{7+}$ stream.

Ethylene and propylene produced in the process is separated and purified on existing (or dedicated) separation trains. The separation(s) can be implemented by any method known to those skilled in the art. This method can be selected from distillation, extraction, absorption, membrane separation, precipitation or crystallization. Preferably, this separation is carried out by one or more fractionation columns.

Unreacted $C_4/C_5$ olefins and any remaining paraffins from the metathesis reactor are separated from the $C_6$ and $C_{7+}$ olefins and recycled back to the dehydrogenation reactor.

The (linear) $C_{7+}$ olefins produced can be further processed for use in chemical applications or as fuels. High purity 1-Hexene is collected from the overheads of a distillation column and remaining 2-hexene and 3-hexene are recycled back to an isomerization reactor.

Using the basic dehydrogenation and metathesis assumptions described above, it was calculated that a 300 kta sized feed stream, in the absence of co-fed ethylene, would yield 105 kta of propylene and 152 kta of 1-hexene, with the balance made up by hydrogen, ethylene and $C_{7+}$ products, as further summarized in Table 2.

TABLE 2

| | | Stream Number | | | | | | |
|---|---|---|---|---|---|---|---|---|
| | | 211 | 217 | 212 | 215 | 216 | 220 | 218 |
| Temperature | C | 50.0 | 17.0 | 101.9 | 27.2 | 93.9 | 90.4 | 120.9 |
| Pressure | BARG | 10.0 | 10.0 | 10.0 | 1.0 | 1.0 | 1.0 | 1.0 |
| Total Mass Rate | T/h | 110.0 | 11.7 | 98.3 | 79.4 | 18.9 | 15.3 | 3.6 |
| Component wt. % | | | | | | | | |
| Ethylene | | 1.1 | 10.5 | 0.0 | 0.0 | 0.0 | 0.0 | 0.0 |
| Propylene | | 9.6 | 89.4 | 0.1 | 0.1 | 0.0 | 0.0 | 0.0 |
| 1-Butene | | 7.6 | 0.1 | 8.5 | 10.5 | 0.0 | 0.0 | 0.0 |
| Butanes | | 19.2 | 0.0 | 21.5 | 26.6 | 0.0 | 0.0 | 0.0 |
| Trans-2-Butene | | 10.0 | 0.0 | 11.2 | 13.9 | 0.0 | 0.0 | 0.0 |
| Cis-2-Butene | | 7.7 | 0.0 | 8.7 | 10.7 | 0.0 | 0.0 | 0.0 |
| 1-Pentene | | 3.3 | 0.0 | 3.7 | 4.6 | 0.0 | 0.0 | 0.0 |
| Pentanes | | 6.4 | 0.0 | 7.2 | 8.9 | 0.0 | 0.0 | 0.0 |
| Trans-2-Pentene | | 12.0 | 0.0 | 13.4 | 16.6 | 0.0 | 0.0 | 0.0 |
| Cis-2-Pentene | | 5.8 | 0.0 | 6.5 | 8.0 | 0.0 | 0.0 | 0.0 |
| Hexenes | | 13.9 | 0.0 | 15.6 | 0.1 | 80.7 | 99.9 | 0.0 |
| $C_{7+}$ | | 3.3 | 0.0 | 3.7 | 0.0 | 19.3 | 0.1 | 100.0 |

FIG. 2 illustrates an exemplary embodiment using a combination of dehydrogenation and metathesis to produce $C_3^=$ and 1-$C_6^=$. A dehydrogenation unit 203 is configured to at least partially dehydrogenate a mixed $C_4$ and $C_5$ alkane stream 201 to generate at least a partial alkene stream 207. The mixed $C_4$ and $C_5$ alkane stream 201 can be a natural gas liquid stream, light ends or complete of the fluid catalytic cracking light cracked naphtha stream or other fluid catalytic cracking product stream, a steam cracker $C_4$ or $C_5$ raffinate stream or a mixed $C_4/C_5$ stream from a biomass source. A natural gas liquid stream can be a NGL derived stream (e.g., a stream that is pretreated by distillation and/or selective hydrogenation/hydrofining to remove feed poisons or isomers. The mixed $C_4$ and $C_5$ alkane stream 201 can include linear and branched alkanes. While the mixed $C_4$ and $C_5$ alkane stream 201 is predominantly such alkanes, it can include other molecules, such as some alkenes. The mixed $C_4$ and $C_5$ alkane stream can include derivative streams from FCC and steam cracking and biomass (e.g., pretreated by distillation and/or selective hydrogenation/hydrofining).

Hydrogen stream 205 can be separated from stream 207 via conventional separation technology, which would be understood by those of ordinary skill in the art. Depending on the specific dehydrogenation technology applied, stream 207 can be optionally pretreated before metathesis to remove (e.g. by selective hydrogenation) any $C_4$ or $C_5$ diolefins from the stream selectively. A metathesis unit 209 is configured to apply metathesis to the alkene stream 207 to generate an effluent 211, wherein the metathesis is optionally conducted in a presence of ethylene 227. The metathesis can be conducted in the presence of ethylene, wherein the amount of ethylene supplied is controlled in order to vary amounts generated of the propylene and 1-hexene. Ethylene can be added to the process from a dedicated feed source (such as steam cracker ethylene or ethylene from ethanol dehydrogenation), or alternatively, any ethylene produced in the metathesis reaction from the metathesis of $C_4/C_5$ feed can be recycled back (e.g. from the cross metathesis of 1-$C_4$ and 1-$C_5$ olefins (and/or propylene)) to the metathesis reactor (for overall net zero ethylene make).

Using the basic dehydrogenation and metathesis assumptions described above, several ethylene co-feeding scenarios were calculated based on a 300 kta sized feed ($C_4/C_5$ and $C_2^=$) stream, as shown in Table 2.

Effluent 211 is fed into a separation unit 213 that is configured to separate the effluent from the metathesis into a $C_4$ and $C_5$ alkane fraction 215, which is optionally recycled back to the dehydrogenating, propylene 217 (or a $C_2^=/C_3^=$ mixed stream that is subsequently separated using conventional separation process, not shown), and 1-hexene 219. Separation unit 213 can include a train of a plurality of distillation columns 213*a*, 213*b*, 213*c* (with effluents 212 and 216 as depicted), and 221. The number of distillation towers depicted in FIG. 2 is merely an example, and other configurations can be used along with the present technological advancement. The plurality of distillation columns can be configured to separate the effluent into a $C_4$-$C_{7+}$ fraction, a $C_6$-$C_{7+}$ fraction, a $C_{7+}$ fraction, and a mixed $C_{6=}$ fraction. The separation unit 213 can include a distillation column 221 that is configured to receive the mixed $C_{6=}$ fraction, wherein the 1-hexene 219 is the overhead stream of the distillation column 221 and 2-hexene and 3-hexene 223 are recycled back to an isomerization reactor 225 and re-isomerized to an equilibrium mixture of 1-hexene, 2-hexene and 3-hexene 226, and recombined with stream 220 for distillation in column 221, as known and understood by those of ordinary skill in the art.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

We claim:

1. A method, comprising:

at least partially dehydrogenating a mixed alkane stream, including at least $C_4$ and $C_5$ alkanes, to generate at least a partial alkene stream and hydrogen;

applying a metathesis reaction to the at least partial alkene stream to generate an effluent, wherein the metathesis reaction is optionally conducted in a presence of ethylene; and separating the effluent from the metathesis reaction into propylene and 1-hexene.

2. The method of claim 1, wherein the metathesis is conducted in the presence of ethylene, and the method further comprises controlling an amount of the ethylene supplied for the metathesis reaction in order to vary amounts generated of the propylene and 1-hexene.

3. The method of claim 1, wherein the metathesis is conducted in the presence of ethylene recycled from a metathesis reactor product stream.

4. The method of claim 1, wherein the metathesis reaction is conducted without co-feeding the ethylene.

5. The method of claim 1, wherein the mixed $C_4$ and $C_5$ alkane stream is a natural gas liquid stream.

6. The method of claim 1, wherein the mixed $C_4$ and $C_5$ alkane stream is the light ends or complete of the fluid catalytic cracking light cracked naphtha stream or other fluid catalytic cracking product stream, a steam cracker $C_4$ or $C_5$ raffinate stream or a mixed $C_4/C_5$ stream from a biomass source.

7. The method of claim 1, wherein the separating includes separating the effluent into a $C_4$-$C_{7+}$ fraction, a $C_6$-$C_{7+}$ fraction, a $C_{7+}$ fraction, and a mixed $C_{6=}$ fraction.

8. The method of claim 6, wherein the method further comprises feeding the $C_{6=}$ fraction to a distillation column, wherein the 1-hexene is overheads of the distillation column and 2-hexene and 3-hexene are recycled back to an isomerization reactor.

9. The method of claim 1, wherein the mixed $C_4$ and $C_5$ alkane stream includes linear and branched alkanes.

10. The method of claim 1, wherein the separating includes generating a $C_4$ and $C_5$ alkane fraction, which is optionally recycled back to the dehydrogenating.

11. A system, comprising:

a dehydrogenation unit configured to at least partially dehydrogenate a mixed alkane stream, including at least $C_4$ and $C_5$ alkanes, to generate at least a partial alkene stream and hydrogen;

a metathesis unit configured to apply a metathesis reaction to the alkene stream to generate an effluent, wherein the metathesis reaction is optionally conducted in a presence of ethylene; and a separation unit configured to separate the effluent from the metathesis reaction into propylene and 1-hexene.

12. The system of claim 11, wherein the separation unit includes a train of a plurality of distililation columns.

13. The system of claim 12, wherein the plurality of distillation columns are configured to separate the effluent into a $C_4$-$C_{7+}$ fraction, a $C_6$-$C_{7+}$ fraction, a $C_{7+}$ fraction, and a mixed $C_{6=}$ fraction.

14. The system of claim 13, wherein the separation unit includes a distillation column configured to receive the mixed $C_{6=}$ fraction, wherein the 1-hexene is overheads of the distillation column and 2-hexene and 3-hexene are recycled back to an isomerization reactor.

15. The system of claim 13, wherein the separation unit generates a $C_4$ and $C_5$ alkane fraction, which is optionally recycled back to the dehydrogenation unit.

* * * * *